US00PP17339P2

(12) United States Plant Patent
Bartels

(10) Patent No.: US PP17,339 P2
(45) Date of Patent: Jan. 2, 2007

(54) ***DELPHINIUM* PLANT NAMED 'BARTHIRTY'**

(50) Latin Name: *Delphinium hybrida*
Varietal Denomination: Barthirty

(75) Inventor: Gosen B. H. Bartels, Aalsmeer (NL)

(73) Assignee: Bartels Breeding B.V., Aalsmeer (NL)

( * ) Notice: Subject to any disclaimer, the term of this patent is extended or adjusted under 35 U.S.C. 154(b) by 0 days.

(21) Appl. No.: 11/146,216

(22) Filed: Jun. 6, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Delphinium* plant named 'Barthirty', characterized by its upright plant habit; freely flowering habit; and double dark violet blue-colored flowers.

1 Drawing Sheet

Botanical designation: *Delphinium hybrida.*
Cultivar denomination: 'Barthirty'.

BACKGROUND OF THE INVENTION

The present Invention relates to a new and distinct cultivar of *Delphinium* plant, botanically known as *Delphinium hybrida*, and hereinafter referred to by the name 'Barthirty'.

The new *Delphinium* is a product of a planned breeding program conducted by the Inventor in Aalsmeer, The Netherlands. The objective of the breeding program was to create new freely-flowering cut flower *Delphinium* cultivars with attractive and unique flower coloration.

The new *Delphinium* originated from a cross-pollination made by the Inventor during the spring of 1994 in Aalsmeer, The Netherlands of a proprietary selection of *Delphinium hybrida* identified as code number 92.306-2, not patented, as the female, or seed, parent with a proprietary selection of *Delphinium hybrida* identified as code number 88.94-12, not patented, as the male, or pollen, parent. The new *Delphinium* was discovered and selected by the Inventor as a flowering plant within the progeny of the stated cross-pollination in a controlled environment in Aalsmeer, The Netherlands in 1997.

Asexual reproduction of the new *Delphinium* by tissue culture in a controlled environment in Aalsmeer, The Netherlands, since 1998, has shown that the unique features of this new *Delphinium* are stable and reproduced true to type in successive generations.

SUMMARY OF THE INVENTION

Plants of the cultivar Barthirty have not been observed under all possible environmental conditions. The phenotype may vary somewhat with variations in environment such as temperature and light intensity without, however, any variance in genotype.

The following traits have been repeatedly observed and are determined to be the unique characteristics of 'Barthirty'. These characteristics in combination distinguish 'Barthirty' as a new and distinct cultivar:

1. Upright plant habit.
2. Freely flowering habit.
3. Double dark violet blue-colored flowers.

Plants of the cultivar Barthirty differ from the parent selections primarily in flower coloration.

Plants of the new *Delphinium* can be compared to plants of the cultivar Odabar, not patented. In side-by-side comparisons conducted in Aalsmeer, The Netherlands, plants of the new *Delphinium* differed from plants of the cultivar Odabar in the following characteristics:

1. Plants of the new *Delphinium* were faster growing than plants of the cultivar Odabar.
2. Leaves of plants of the new *Delphinium* had shorter petioles than leaves of plants of the cultivar Odabar.
3. Plants of the new *Delphinium* had shorter inflorescences with fewer flowers per inflorescence than plants of the cultivar Odabar.
4. Plants of the new *Delphinium* and the cultivar Odabar differed in flower coloration.

BRIEF DESCRIPTION OF THE PHOTOGRAPH

The accompanying colored photograph illustrates the overall appearance of the new *Delphinium*, showing the colors as true as it is reasonably possible to obtain in colored reproductions of this type. Colors in the photograph may differ slightly from the color values cited in the detailed botanical description which accurately describe the colors of the new *Delphinium*. The photograph comprises a side perspective view of three typical flowering stems of 'Barthirty'.

DETAILED BOTANICAL DESCRIPTION

In the following description, color references are made to The Royal Horticultural Society Colour Chart, 1995 Edition, except where general terms of ordinary dictionary significance are used. Plants used for the photograph and the following description were about nine months old and grown in a glass-covered greenhouse and cultural conditions which closely approximate commercial production conditions in Aalsmeer, The Netherlands. During the production of the plants, day temperatures were about 20° C. and night temperatures were about 10 to 15° C.

Botanical classification: *Delphinium hybrida* cultivar Barthirty.

Parentage:

*Female parent.*—Proprietary selection of *Delphinium hybrida* identified as code Number 92.306-2, not patented.

*Male parent.*—Proprietary selection of *Delphinium hybrida* identified as code Number 88.94-12, not patented.

Propagation:

*Type cutting.*—By tissue culture.

*Time to initiate roots.*—About four weeks at 9° C.

*Root description.*—Thick.

Plant description:

*Form.*—Upright perennial flowering plant with double flowers arranged on racemes; numerous flower racemes per plant; vigorous growth habit.

*Plant height.*—About 80 to 150 cm.

*Plant diameter.*—About 40 cm.

*Primary flowering stems.*—Quantity: About three to five per plant. Length: About 80 to 150 cm. Diameter: About 1 to 1.5 cm. Internode length: About 4 to 5 cm. Strength: Strong. Texture: Smooth, glabrous; somewhat waxy. Color: 139C tinted with 46A.

*Foliage description.*—Arrangement: Alternate; simple. Length: About 12 to 16 cm. Width: About 12 to 20 cm. Shape: Palmately-lobed. Apex: Acute. Base: Rounded, cordate. Margin: Serrate. Texture, upper and lower surfaces: Smooth, glabrous; fleshy. Venation pattern: Palmate. Color: Developing and fully expanded foliage, upper surface: 137A. Developing and fully expanded foliage, lower surface: 138B. Venation, upper surface: 144A. Venation, lower surface: 138B. Petiole: Length: About 8 to 11 cm. Diameter: About 3 mm. Texture, upper and lower surfaces: Smooth, glabrous. Color: 139C tinted with 46A.

Flower description:

*Appearance.*—Double flowers arranged in terminal racemes; flowers zygomorphic. Flowers face mostly outward. Flowers persistent.

*Quantity of flowers per raceme.*—About 35 to 45.

*Natural flowering season.*—Flowering continuous from June through September in The Netherlands.

*Fragrance.*—None detected.

*Flower longevity on the plant.*—About 10 to 14 days.

*Flower longevity as a cut flower.*—About ten days.

*Inflorescence size.*—Length: About 40 to 50 cm. Diameter: About 15 to 20 cm.

*Flower size.*—Diameter: About 6 cm. Depth: About 1.5 cm.

*Flower buds.*—Length: About 2 cm. Diameter: About 1.6 cm. Shape: Ovate. Color: 84A.

*Petals/petaloids.*—Appearance/arrangement: About 15 petals and petaloids arranged in several whorls. Length: About 3.2 cm. Width: About 2.1 to 3 cm. Shape: Oblanceolate. Apex: Rounded. Base: Roughly obtuse. Margin: Entire to serrulate. Texture: Smooth, glabrous. Color: When opening, upper and lower surfaces: 89C to 90C. Fully opened, upper and lower surfaces: 89A to 90A; color becoming closer to 79B with development.

*Sepals.*—None observed.

*Pedicels.*—Length: About 7 to 9 cm. Diameter: About 1.5 mm. Angle: About 30° from vertical. Strength: Strong. Texture: Smooth, glabrous. Color: 139C.

*Reproductive organs.*—Stamens: Quantity per flower: About 28 to 34. Anther length: About 2 mm. Anther shape: Ovate. Anther color: 202A. Pollen amount: Scare. Color: 155A. Pistils: Quantity per flower: About five. Pistil length: About 8 mm. Stigma shape: Rounded. Stigma color: 155A. Style length: About 4 mm. Style color: 155A. Ovary color: 144B.

*Seed/fruit.*—Seed and fruit development has not been observed.

Disease/pest resistance: Plants of the new *Delphinium* have not been noted to be resistant to pathogens and pests common to *Delphinium*.

Low temperature tolerance: Plants of the new *Delphinium* have been observed to tolerate low temperatures down to −5° C.

It is claimed:

1. A new and distinct cultivar of *Delphinium* plant named 'Barthirty', as illustrated and described.

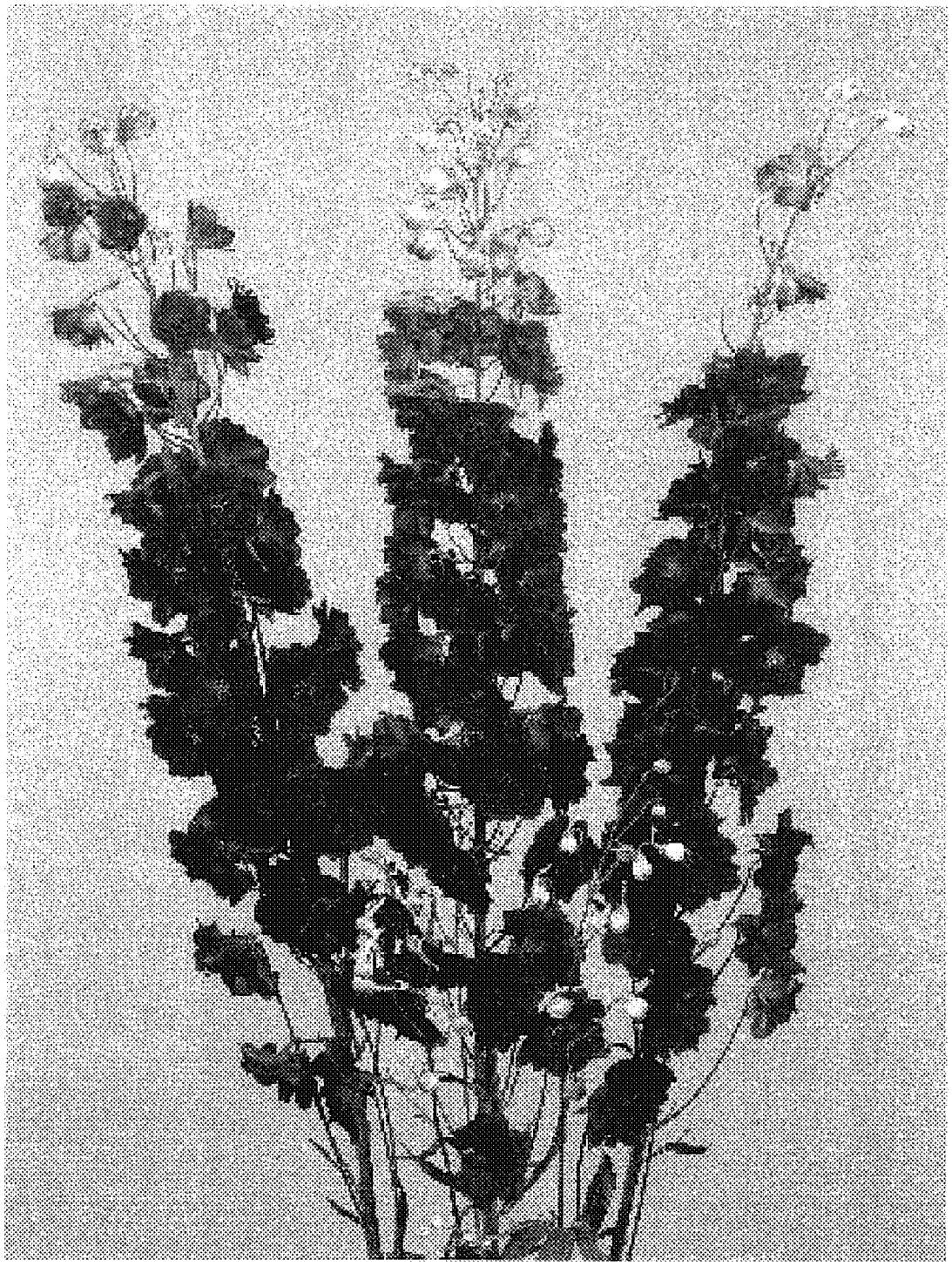

* * * * *